United States Patent
DeLucia et al.

(10) Patent No.: US 7,422,712 B2
(45) Date of Patent: Sep. 9, 2008

(54) TECHNIQUE FOR INCORPORATING A LIQUID ADDITIVE INTO A NONWOVEN WEB

(75) Inventors: Mary Lucille DeLucia, Roswell, GA (US); Braulio Polanco, Roswell, GA (US); Peter Kobylivker, Marietta, GA (US); Ali Yahiaoui, Roswell, GA (US); Tamara Lee Mace, Marietta, GA (US); Stephen Avedis Baratian, Roswell, GA (US); Steven R. Stopper, Duluth, GA (US); Charles E. Edmundson, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 85 days.

(21) Appl. No.: 11/304,988

(22) Filed: Dec. 15, 2005

(65) Prior Publication Data
US 2007/0141941 A1    Jun. 21, 2007

(51) Int. Cl.
*D01F 1/10* (2006.01)
*D04H 3/00* (2006.01)
(52) U.S. Cl. ...................... 264/103; 264/211
(58) Field of Classification Search ............. 264/103, 264/211
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,423,266 A | 1/1969 | Davies et al. | |
| 3,494,821 A | 2/1970 | Evans | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |

(Continued)

FOREIGN PATENT DOCUMENTS

EP    0539890 A1    5/1993

(Continued)

OTHER PUBLICATIONS

Article—*Adsorption of Gases in Multimolecular Layers*, Brunauer et al., The Journal of the American Cancer Society, vol. 60, Jan.-Jun. 1938, pp. 309-319.

(Continued)

*Primary Examiner*—Leo B Tentoni
(74) *Attorney, Agent, or Firm*—Dority & Manning, P.A.

(57) ABSTRACT

A technique for incorporating a liquid additive into a nonwoven web is disclosed. Specifically, the liquid additive is loaded into filler particles to form a "dry liquid concentrate", i.e., pulverulent granular solid or powder loaded with the liquid additive. The incorporation of the liquid additive into dry liquid concentrates provides a variety of benefits. For example, prior to extrusion, the dry liquid concentrates generally retain the properties of filler particles from which they are formed as the liquid remains isolated. In this manner, a higher level of the liquid additive may be compounded with a melt-extrudable base composition without adversely affecting the extrusion process. Only upon extrusion of the composition will a significant portion of the liquid additive be released to provide the desired properties to the resulting nonwoven web.

27 Claims, 3 Drawing Sheets

U.S. PATENT DOCUMENTS

| | | | |
|---|---|---|---|
| 3,849,241 A | 11/1974 | Butin et al. | |
| 3,855,046 A | 12/1974 | Hansen et al. | |
| 3,951,824 A | 4/1976 | Maxson et al. | |
| 4,041,203 A | 8/1977 | Brock et al. | |
| 4,062,693 A | 12/1977 | Berger | |
| 4,116,909 A | 9/1978 | Muller | |
| 4,144,370 A | 3/1979 | Boulton | |
| 4,323,534 A | 4/1982 | DesMarais | |
| 4,340,563 A | 7/1982 | Appel et al. | |
| 4,341,213 A | 7/1982 | Cohen | |
| 4,374,888 A | 2/1983 | Bornslaeger | |
| 4,535,113 A | 8/1985 | Foster et al. | |
| 4,579,779 A | 4/1986 | Ohno | |
| 4,652,487 A | 3/1987 | Morman | |
| 4,655,760 A | 4/1987 | Morman et al. | |
| 4,657,802 A | 4/1987 | Morman | |
| 4,663,220 A | 5/1987 | Wisneski et al. | |
| 4,720,415 A | 1/1988 | Vander Wielen et al. | |
| 4,766,029 A | 8/1988 | Brock et al. | |
| 4,781,966 A | 11/1988 | Taylor | |
| 4,789,699 A | 12/1988 | Kieffer et al. | |
| 4,834,738 A | 5/1989 | Kielpikowski et al. | |
| 4,857,593 A | 8/1989 | Leung et al. | |
| 4,920,168 A | 4/1990 | Nohr et al. | |
| 4,925,890 A | 5/1990 | Leung et al. | |
| 4,931,492 A | 6/1990 | Foster et al. | |
| 4,965,122 A | 10/1990 | Morman | |
| 4,981,747 A | 1/1991 | Morman | |
| 5,003,023 A | 3/1991 | Foster et al. | |
| 5,093,422 A | 3/1992 | Himes | |
| 5,114,781 A | 5/1992 | Morman | |
| 5,116,662 A | 5/1992 | Morman | |
| 5,120,888 A | 6/1992 | Nohr et al. | |
| 5,169,706 A | 12/1992 | Collier, IV et al. | |
| 5,213,881 A | 5/1993 | Timmons et al. | |
| 5,226,992 A | 7/1993 | Morman | |
| 5,272,236 A | 12/1993 | Lai et al. | |
| 5,278,272 A | 1/1994 | Lai et al. | |
| 5,284,703 A | 2/1994 | Everhart et al. | |
| 5,304,599 A | 4/1994 | Himes | |
| 5,332,613 A | 7/1994 | Taylor et al. | |
| 5,336,545 A | 8/1994 | Morman | |
| 5,344,862 A * | 9/1994 | Nohr et al. | 524/269 |
| 5,382,400 A | 1/1995 | Pike et al. | |
| 5,385,775 A | 1/1995 | Wright | |
| 5,414,470 A | 5/1995 | Hotta et al. | |
| 5,439,623 A | 8/1995 | Fintel | |
| 5,464,688 A | 11/1995 | Timmons et al. | |
| 5,494,855 A | 2/1996 | Nohr et al. | |
| 5,500,223 A | 3/1996 | Behan et al. | |
| 5,516,814 A | 5/1996 | Trotoir | |
| 5,539,056 A | 7/1996 | Yang et al. | |
| 5,596,052 A | 1/1997 | Resconi et al. | |
| 5,620,779 A | 4/1997 | Levy et al. | |
| D390,708 S | 2/1998 | Brown | |
| 5,744,548 A | 4/1998 | Nohr et al. | |
| 5,962,112 A | 10/1999 | Haynes et al. | |
| 5,985,953 A | 11/1999 | Lightsey et al. | |
| 6,005,027 A | 12/1999 | Guillet et al. | |
| D428,267 S | 7/2000 | Romano, III et al. | |
| 6,093,665 A | 7/2000 | Sayovitz et al. | |
| 6,203,889 B1 | 3/2001 | Quincy, III et al. | |
| 6,312,639 B1 | 11/2001 | Ertle et al. | |
| 6,315,864 B2 | 11/2001 | Anderson et al. | |
| 6,323,389 B1 | 11/2001 | Thomas et al. | |
| 6,653,524 B2 | 11/2003 | DeLucia et al. | |
| 6,924,320 B2 | 8/2005 | Morriston | |
| 6,969,441 B2 | 11/2005 | Welch et al. | |
| 6,995,202 B2 | 2/2006 | Lake, Jr. et al. | |
| 7,101,623 B2 | 9/2006 | Jordan et al. | |
| 2002/0115970 A1 | 8/2002 | Steffen et al. | |
| 2003/0222374 A1 | 12/2003 | Castellari et al. | |
| 2004/0116018 A1 | 6/2004 | Fenwick et al. | |
| 2004/0142170 A1 | 7/2004 | Prabhu et al. | |
| 2005/0118435 A1 | 6/2005 | DeLucia et al. | |
| 2005/0119410 A1 | 6/2005 | DeLucia et al. | |
| 2005/0137313 A1 | 6/2005 | Wong et al. | |
| 2005/0209373 A1 | 9/2005 | Zucker | |
| 2005/0233074 A1 | 10/2005 | Dalziel et al. | |
| 2005/0233150 A1 | 10/2005 | Jing et al. | |

FOREIGN PATENT DOCUMENTS

| | | |
|---|---|---|
| EP | 0591676 A1 | 5/1994 |
| WO | WO 0134086 A1 | 5/2001 |
| WO | WO 110747 A2 | 11/2005 |
| WO | WO 111120 A1 | 11/2005 |

OTHER PUBLICATIONS

American Society for Testing Materials (ASTM) Designation: D1238-95, "Standard Test Method for Flow Rates of Thermoplastics by Extrusion Plastometer," pp. 273-281, published Jan. 1996.

American Society for Testing Materials (ASTM) Designation: D445-04, "Standard Test Method for Kinematic Viscosity of Transparent and Opaque Liquids (and the Calculation of Dynamic Viscosity)," pp. 1-10, published Jun. 2004.

GE Advanced Materials Silicones product information—*Silquest PA-1 Organosilicone*, pp. 1-6, published Mar. 2005.

Natrochem, Inc. Bulletin—*Powders (DLC)*, pp. 2-5, published Jan. 2005.

Kenrich Petochemicals, Inc. MSDS Product Name Ken-React® LICA® 12—published Jan. 7, 2003.

Kenrich Petochemicals, Inc. MSDS Product Name Ken-React® LICA® 01—published Apr. 14, 2003.

Omya Inc. MSDS Product Name OMYACARB® 1 SS T—FL—published Dec. 9, 2004.

Dow Corning Product Information MB50-001 Masterbatch, undated.
Dow Corning Product Information MB50-321 Masterbatch, undated.
Dow Corning Product Information MB25-513 Masterbatch, undated.
Search Report and Written Opinion for PCT/US2006/033332, Jan. 10, 2007.

* cited by examiner

TECHNIQUE FOR INCORPORATING A LIQUID ADDITIVE INTO A NONWOVEN WEB

BACKGROUND OF THE INVENTION

Nonwoven webs are currently employed in a variety of disposable absorbent articles, such as diapers, incontinent products, feminine care products, wipes, towels, sterilization wraps, medical drapes, medical garments, and industrial workwear. The nonwoven webs may be utilized as a single layer or as a component of a multilayered laminate or composite. To improve the performance of a nonwoven web, the characteristics of the fibers used to form the web are sometimes modified with a liquid additive. A wide variety of liquid additives are commonly employed for this purpose, including repellents, wetting agents, tackifiers, adhesives, flame retardants, antistatic agents, stabilizers, colorants, inks, etc. Although various techniques may be utilized to incorporate the liquid additives into the web, it is normally desired that they are compounded with the thermoplastic composition prior to melt extrusion to improve processing efficiency and distribution uniformity. For instance, hydrophobic polyolefin compositions are often compounded with liquid siloxanes to improve the wettability or softness of the resulting fibers. Unfortunately, however, the extent to which liquid additives may be loaded into the thermoplastic composition is often limited. Specifically, it is relatively difficult to compound thermoplastic compositions at high liquid additive levels.

As such, a need currently exists for an improved method of incorporating a liquid additive into a thermoplastic composition used to form a nonwoven web.

SUMMARY OF THE INVENTION

A method for forming a nonwoven web is disclosed. The method comprises compounding a masterbatch with a base composition to form a blend; melt extruding the blend to form fibers; and depositing the fibers onto a forming surface. The masterbatch comprises a plurality of dry liquid concentrates blended with a carrier resin. The dry liquid concentrates constitute from about 20 wt. % to about 80 wt. % of the masterbatch. Further, the dry liquid concentrates are formed from filler particles loaded with a liquid additive, the liquid additive constituting from about 10 wt. % to about 80 wt. % of the dry liquid concentrates.

In accordance with another embodiment of the present invention, a nonwoven web is disclosed that comprises fibers formed by melt-extrusion of a polymer blend. The polymer blend contains a plurality of dry liquid concentrates, a carrier resin, and a base composition. The dry liquid concentrates are formed from filler particles loaded with a liquid additive, the liquid additive constituting from about 0.0003 wt. % to about 10 wt. % of the blend.

Other features and aspects of the present invention are described in more detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figure in which.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "fibers" encompasses both fibers of a staple length and those that are substantially continuous (e.g., filaments), and likewise includes monocomponent, multicomponent (e.g., bicomponent), monoconstituent, multiconstituent (e.g., biconstituent) fibers, etc.

As used herein the term "nonwoven fabric or web" generally refers to a web having a structure of individual fibers or threads which are interlaid, but not in an identifiable manner as in a knitted fabric. Examples of suitable nonwoven fabrics or webs include, but are not limited to, meltblown webs, spunbond webs, carded webs, etc. The basis weight of the nonwoven webs may generally vary, but is typically from about 5 grams per square meter ("gsm") to 200 gsm, in some embodiments from about 10 gsm to about 150 gsm, and in some embodiments, from about 15 gsm to about 100 gsm.

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 micrometers in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. Nos. 4,340,563 to Appel, et al., 3,692,618 to Dorschner, et al., 3,802,817 to Matsuki, et al., 3,338,992 to Kinney, 3,341,394 to Kinney, 3,502,763 to Hartman, 3,502,538 to Levy, 3,542,615 to Dobo, et al., and 5,382,400 to Pike, et al., which are incorporated herein in their entirety by reference thereto for all purposes. Spunbond fibers are generally not tacky when they are deposited onto a collecting surface. Spunbond fibers may sometimes have diameters less than about 40 micrometers, and are often between about 5 to about 20 micrometers.

As used herein the terms "extensible" or "extensibility" generally refers to a material that stretches or extends in the direction of an applied force by at least about 50% of its relaxed length or width. An extensible material does not necessarily have recovery properties. For example, an elastomeric material is an extensible material having recovery properties. A meltblown web may be extensible, but not have recovery properties, and thus, be an extensible, non-elastic material.

As used herein, the term "elastomeric" or "elastic" refers to a material that, upon application of a stretching force, is stretchable in at least one direction (such as the CD direction), and which upon release of the stretching force, contracts/returns to approximately its original dimension. For example, a stretched material may have a stretched length that is at least 50% greater than its relaxed unstretched length, and which will recover to within at least 50% of its stretched length upon release of the stretching force. A hypothetical example would be a one (1) inch sample of a material that is stretchable to at least 1.50 inches and which, upon release of the stretching force, will recover to a length of not more than 1.25 inches. Desirably, such elastomeric sheet contracts or recovers at least 50%, and even more desirably, at least 80% of the stretch length in the cross machine direction.

DETAILED DESCRIPTION

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Generally speaking, the present invention is directed to a technique for incorporating a liquid additive into a nonwoven web. Specifically, the liquid additive is loaded into filler particles to form a "dry liquid concentrate", i.e., pulverulent granular solid or powder loaded with the liquid additive. The incorporation of the liquid additive into dry liquid concentrates provides a variety of benefits. For example, prior to extrusion, the dry liquid concentrates generally retain the properties of filler particles from which they are formed as the liquid remains isolated. In this manner, a higher level of the liquid additive may be compounded with a melt-extrudable base composition without adversely affecting the extrusion process. Only upon extrusion of the composition will a significant portion of the liquid additive be released to provide the desired properties to the resulting nonwoven web.

Any of a variety of filler particles may be used to form the dry liquid concentrates in accordance with the present invention, such as inorganic particles, e.g., silica, alumina, zirconia, magnesium oxide, titanium dioxide, iron oxide, zinc oxide, zeolites, silicates, titanates, zirconates, clays (e.g., smectite or bentonite), calcium carbonate, and barium sulfate; organic particles, e.g., carbon black and organic pigments; and so forth. In one particular embodiment, the filler particles are formed from a silicon oxide compound, such as silica, a metal silicate, etc. Silicon oxides exist with varying degrees of crystallinity, from fully crystalline to amorphous, and may be derived from both natural sources (e.g., diatomaceous earth) and synthetic sources. The silica particles may contain silanol surface groups that react with certain additives, such as organopolysiloxanes, to enhance the loading efficiency. Suitable silica particles are commercially available from and Natrochem, Inc. of Savannah, Ga. under the designation DLC® and PPG Industries Inc. under the designations HiSil® ABS, HiSil® 210, HiSil® 233 and HiSil® 243.

The filler particles may possess various forms, shapes, and sizes depending upon the desired result, such as a sphere, crystal, rod, disk, tube, string, etc. The average size of the particles may be less than about 500 micrometers, in some embodiments less than about 100 micrometers, in some embodiments less than about 100 nanometers, in some embodiments from about 1 to about 50 nanometers, in some embodiments from about 2 to about 50 nanometers, and in some embodiments, from about 4 to about 20 nanometers. The particles may also have a high surface area, such as from about 50 square meters per gram ($m^2/g$) to about 1000 $m^2/g$, in some embodiments from about 60 $m^2/g$ to about 600 $m^2/g$, and in some embodiments, from about 100 $m^2/g$ to about 250 $m^2/g$. Surface area may be determined by the physical gas adsorption (B.E.T.) method of Bruanauer, Emmet, and Teller, Journal of American Chemical Society, Vol. 60, 1938, p. 309, with nitrogen as the adsorption gas. Without intending to be limited by theory, it is believed that particles having such a small size and high surface area may have improved loading capacity for the liquid additive.

Regardless of the particles selected, they are loaded with a liquid additive in accordance with the present invention to form dry liquid concentrates. The liquid additive may be a liquid at room temperature or simply heated above its melting temperature prior to and/or during the loading process to obtain a desired loading viscosity. For example, the liquid additive may have a kinematic viscosity of from about 1 to about 150,000 centistokes, in some embodiments from about 250 to about 70,000 centistokes, and in some embodiments, from about 500 to about 10,000 centistokes. The kinematic viscosity is the absolute viscosity of the additive divided by its density at the same temperature of measurement, and is determined according to ASTM D445 at 25° C. In some cases, liquid additives with such a viscosity may also provide mobility so that the additive is capable of migrating to the polymer surface.

A wide variety of liquid additive types may be employed in the present invention to improve the properties of the resulting nonwoven webs. Suitable liquids additives for nonwoven web applications include, for example, solvent repellents, wetting agents, skin care additives, flame retardants, antistatic agents, stabilizers, fragrances, colorants, processing aids, and other compounds. Skin care additives, for example, are widely known and used in the art for providing skin wellness benefits and to address or prevent particular skin disorders or irritating conditions, including pain, itching, chapping, inflammation, and other skin disorders. One suitable class of skin care additives includes emollients, such as oils (e.g., petroleum based oils, vegetable based oils, mineral oils, natural or synthetic oils, silicone oils, lanolin and lanolin derivatives, kaolin and kaolin derivatives, and so forth); esters (e.g., cetyl palmitate, stearyl palmitate, cetyl stearate, isopropyl laurate, isopropyl myristate, isopropyl palmitate, and so forth); glycerol esters; ethers (e.g., eucalyptol, cetearyl glucoside, dimethyl isosorbicide polyglyceryl-3 cetyl ether, polyglyceryl-3 decyltetradecanol, propylene glycol myristyl ether, and so forth); alkoxylated carboxylic acids; alkoxylated alcohols; fatty alcohols (e.g., octyidodecanol, lauryl, myristyl, cetyl, stearyl and behenyl alcohol, and so forth); etc.

One particularly suitable skin care additive includes dimethicones, which are polydimethylsiloxane compounds having the general formula $CH_3[Si(CH_3)_2O]_xSi(CH_3)_3$ and includes mixtures of fully methylated linear siloxane polymers end blocked with trimethylsiloxy units.

Another useful liquid additive is an organopolysiloxane processing aid, which may coat the metal surface of melt-processing equipment and enhance ease of processing. One example of a suitable organopolysiloxane liquid additive that may be used in the present invention has the following general formula:

wherein, $x \geq 1$;

$y \geq 0$; and each R is individually selected from the group consisting of unsubstituted and substituted monovalent hydrocarbon groups containing from 1 to 20 carbon atoms. Some examples of such silicon atom-bonded, substituted or unsubstituted, monovalent hydrocarbon groups represented by "R" include alkyl groups (e.g., methyl, ethyl, propyl, isopropyl, butyl, isobutyl, tert-butyl, pentyl, neopentyl, hexyl, cyclohexyl, octyl, nonyl and decyl); aryl groups (e.g., phenyl, tolyl, xylyl and naphthyl); aralkyl groups (e.g., benzyl, phenylethyl, and phenylpropyl); alkenyl groups (e.g., vinyl, allyl, propenyl, isopropenyl, butenyl, hexenyl, cyclohexenyl and octenyl); and derivatives of the foregoing groups in which some or all of the hydrogen atoms are substituted with halogen atoms (e.g., chloromethyl, chloropropyl, bromoethyl, and trifluoropropyl); cyano groups (e.g., cyanoethyl); hydroxyl groups, ester groups, etc.

In most cases, the organopolysiloxane contains at least two unsaturated functional groups to facilitate crosslinking. Particularly desired unsaturated functional groups are alkenyl groups. The alkyenyl groups typically contain from 2 to 12 carbon atoms and are represented by the following general formula:

wherein, $R_1$ is a single bond or an alkylene group containing from 2 to 10 carbon atoms. The alkylene group may be linear or branched. Some examples of alkenyl groups include vinyl, 2-propenyl, 3-butenyl, 5-hexenyl, 7-octenyl and 10-undecenyl. The organopolysiloxanes generally contain an average of at least 0.5, in some embodiments at least 1, and in some embodiments, at least 2 alkenyl groups per molecule. Likewise, the content of alkenyl groups is typically from about 0.0001 to about 20 mol %, in some embodiments from about 0.001 to 10 mol %, and in some embodiments, from about 0.01 to 5 mol % of the entire "R" groups. The alkenyl groups may be bonded to silicon atoms at one or more ends of the molecular chain ("terminal") and/or to silicon atoms within the molecular chain. It is normally desired that at least two alkenyl groups are located at the terminals of the molecular chain to reduce the likelihood that steric hindrance will inhibit the crosslinking reaction. One particular example of such an alkenyl-containing organopolysiloxane is set forth below:

wherein, each $R_2$ is individually selected from unsubstituted and substituted monovalent hydrocarbon groups containing from 1 to 20 carbon atoms;

each $R_3$ is individually selected from unsubstituted and substituted alkenyl groups containing from 1 to 20 carbon atoms;

$x \geq 1$; and $y \geq 0$ and is selected so that the molecule contains an average of at least two alkenyl groups per molecule. Preferably, $R_2$ is an unsubstituted monovalent hydrocarbon group having less than 7 carbon atoms or a halogenated alkyl group having less than 7 carbon atoms. For example, $R_2$ may be an alkyl group (e.g., methyl or ethyl); a cycloalkyl group (e.g., cyclohexyl); an aryl group (e.g., phenyl); or derivatives of the foregoing groups in which some or all of the hydrogen atoms are substituted with halogen atoms (e.g., chloromethyl, chloropropyl, bromoethyl, and trifluoropropyl); cyano groups (e.g., cyanoethyl); hydroxyl groups, ester groups, etc.

In one embodiment of the present invention, one or more organopolysiloxanes are employed that are vinyl-terminated and have the following general formula:

wherein, each $R_2$ is individually selected from unsubstituted and substituted monovalent hydrocarbon groups containing from 1 to 20 carbon atoms; and x is from 100 to 1200.

The organopolysiloxanes may contain at least about 5 mol %, in some embodiments from about 5 mol % to about 50 mol %, and in some embodiments, from about 10% to about 30 mol % of diphenylsiloxane units in the diorganosiloxane units of which the backbone is constructed, based on the entire base polymer. In addition or alternatively, the organopolysiloxanes may contain at least about 10 mol %, in some embodiments from about 10 mol % to about 50 mol %, and in some embodiments, from about 25% to about 35 mol % of methylphenylsiloxane units in the diorganosiloxane units of which the backbone is constructed, based on the entire base polymer. Some examples of suitable organopolysiloxanes include dimethylvinylsiloxy end group-capped polydimethylsiloxane, methyldivinylsiloxy end group-capped polydimethylsiloxane, dimethylvinylsiloxy end group-capped dimethylsiloxane (80 mol %)/methylphenylsiloxane (20 mol %) copolymers, dimethylvinylsiloxy end group-capped dimethylsiloxane (80 mol %)/diphenylsiloxane (20 mol %) copolymers, dimethylvinylsiloxy end group-capped dimethylsiloxane (90 mol %)/diphenylsiloxane (10 mol %) copolymers, and trimethylsiloxy end group-capped dimethylsiloxane/methylvinylsiloxane copolymers. Besides the above-mentioned polymers, other polymers may also be utilized in the present invention. For instance, some suitable vinyl-modified silicones include, but are not limited to, vinyldimethyl terminated polydimethylsiloxanes; vinylmethyl, dimethylpolysiloxane copolymers; vinyidimethyl terminated vinylmethyl, dimethylpolysiloxane copolymers; divinylmethyl terminated polydimethylsiloxanes; polydimethylsiloxane, mono vinyl, mono n-butyldimethyl terminated; and vinylphenylmethyl terminated polydimethylsiloxanes. Further, some methyl-modified silicones that can be used include, but are not limited to, dimethylhydro terminated polydimethylsiloxanes; methylhydro, dimethylpolysiloxane copolymers; methylhydro terminated methyloctyl siloxane copolymers; and methylhydro, phenylmethyl siloxane copolymers.

Other examples of suitable polyorganosiloxanes are described in U.S. Pat. Nos. 4,535,113; 4,857,593; 4,925,890; 4,931,492; and 5,003,023, which are incorporated herein in their entirety by reference thereto for all purposes. A particular suitable organopolysiloxane is SILQUEST® PA-1, which is commercially available from GE Silicones.

Any known method for loading a liquid additive into a filler particle may generally be employed in the present invention. For example, the liquid additive may simply be blended together with particles until the desired flowability characteristics are achieved. Other suitable loading techniques are described in more detail in U.S. Pat. Nos. 3,951,824 to Maxson, et al.; 4,579,779 to Ohno; 5,500,223 to Behan, et al., as well as U.S. Patent Application Publication No. 2005/0233074 to Dalziel, et al., all of which are incorporated herein in their entirety by reference thereto for all purposes. Regardless of the loading technique employed, however, it is generally desired that the liquid additive constitute a substantial component of the resulting dry liquid concentrate. For example, the liquid additive typically constitutes from about 10 wt. % to about 80 wt. %, in some embodiments from about 20 wt. % to about 60 wt. %, and in some embodiments, from about 25 wt. % to about 50 wt. % of the dry liquid concentrate. Likewise, the filler particles typically constitute from about 20 wt. % to about 90 wt. %, in some embodiments from about 40 wt. % to about 80 wt. %, and in some embodiments, from about 50 wt. % to about 75 wt. % of the dry liquid concentrate. Even when loaded at such high levels, the concentrates possess a flowability characteristic that is substantially similar to the unloaded form of the filler particles. This enables the concentrates to be handled and processed similar to bulk solid powders, i.e., without significant clumping or pasting, and thus be readily compounded with thermoplastic compositions in accordance with the present invention.

Generally speaking, the dry liquid concentrates are blended with a carrier resin to form a masterbatch. Among other things, the carrier resin enhances the compatibility of the dry liquid concentrate with the base composition used to form the nonwoven web. Without intending to be limited by theory, the present inventors believe that the liquid additive is more miscible with amorphous regions of a polymer than the crystalline regions. Thus, the carrier resin employed in the masterbatch is generally amorphous or semicrystalline to optimize compatibility with the dry liquid concentrate. The amorphous state is considered to be a randomly tangled mass of polymer chains. Amorphous polymers may have an X-ray diffraction pattern of a diffuse halo, which indicates no regularity in the polymer structure. Amorphous polymers also show softening behaviors at the glass transition temperature, but no true melt or first order transition. The semicrystalline state of polymers is one in which long segments of the polymer chains appear in both amorphous and crystalline states or phases. The crystalline phase contains multiple lattices in which the polymer chain assumes a chain-folded conformation (lamellae) in which there is a highly ordered registry in adjacent folds of the various chemical moieties of which the chain is constructed. The packing arrangement (short order orientation) within the lattice is highly regular in both its chemical and geometric aspects. Semicrystalline polymers show characteristic melting points, above which the crystalline lattices become disordered and rapidly lose their identity. Either concentric rings or a symmetrical array of spots, which are indicative of the nature of the crystalline order, generally distinguishes the X-ray diffraction pattern of semicrystalline polymers (or copolymers).

Exemplary amorphous polymers include polystyrene, polycarbonate, acrylic, acrylonitrile-butadiene-styrene (ABS), styrene-acrylonitrile, and polysulfone. Exemplary semicrystalline polymers include high and low density polyethylene, polypropylene, polyoxymethylene, poly(vinylidine fluoride), poly(methyl pentene), poly(ethylene-chlorotrifluoroethylene), poly(vinyl fluoride), poly(ethylene oxide), poly(ethylene terephthalate), poly(butylene terephthalate), nylon 6, nylon 66, poly(vinyl alcohol) and polybutene. Particularly desired semicrystalline polymers are predominantly linear polymers having a regular structure. Examples of semi-crystalline, linear polymers that may be used in the present invention include polyethylene, polypropylene, blends of such polymers and copolymers of such polymers.

Semi-crystalline propylene-based polymers, for instance, may be used that have a melt flow rate of from about 5 grams per 10 minutes to about 50 grams per 10 minutes. Melt flow rate is the weight of a polymer (in grams) that may be forced through an extrusion rheometer orifice (0.0825-inch diameter) when subjected to a force of 2160 grams in 10 minutes at 230° C., measured in accordance with ASTM Test Method D1238-E. The propylene-based semi-crystalline polymers may also have a density of from about 0.87 to about 0.92 g/cm$^3$, and in some embodiments, from about 0.89 to about 0.90 g/cm$^3$. Exemplary semi-crystalline polypropylenes may include ExxonMobil PP3155, PP1074KN, PP9074MED, Dow 6D43, and Pro-fax™ 6301 (Basell North America, Inc.).

Semi-crystalline ethylene-based polymers may also be suitable for use in the carrier resin that have a melt flow index of from about 5 grams per 10 minutes to about 50 grams per 10 minutes. Melt flow index is the weight of a polymer (in grams) that may be forced through an extrusion rheometer orifice (0.0825-inch diameter) when subjected to a force of 2160 grams in 10 minutes at 190° C., measured in accordance with ASTM Test Method D1238-E. Such ethylene-based polymers may also have a density of greater than about 0.910 grams per cubic centimeter (g/cm$^3$), in some embodiments greater than about 0.915 g/cm$^3$, in some embodiments from about 0.915 to about 0.960 g/cm$^3$, and in some embodiments, from about 0.917 and 0.960 g/cm$^3$. Exemplary ethylene-based polymers include DOWLEX™ 2517; Dow LLDPE DNDA-1082, Dow LLDPE DNDB-1077, Dow LLDPE 1081, and Dow LLDPE DNDA 7147. In some instances, higher density polymers may be useful, such as Dow HDPE DMDA-8980.

The amount of the carrier resin employed will generally depend on a variety of factors, such as the type of carrier resin and base composition, the type of particles and liquid additive, the processing conditions, etc. Typically, the carrier resin constitutes from about 20 wt. % to about 80 wt. %, in some embodiments from about 30 wt. % to about 70 wt. %, and in some embodiments, from about 40 wt. % to about 60 wt. % of the masterbatch. The dry liquid concentrates likewise normally constitute from about 20 wt. % to about 80 wt. %, in some embodiments from about 30 wt. % to about 70 wt. %, and in some embodiments, from about 40 wt. % to about 60 wt. % of the masterbatch. The liquid additive also normally constitutes from about 5 wt. % to about 60 wt. %, in some embodiments from about 10 wt. % to about 50 wt. %, and in some embodiments, from about 20 wt. % to about 40 wt. % of the masterbatch.

The carrier resin may be blended with the dry liquid concentrates using any known technique, such as batch and/or continuous compounding techniques that employ, for example, a Banbury mixer, Farrel continuous mixer, single screw extruder, twin screw extruder, etc. If desired, the carrier resin and dry liquid concentrates may be dry blended. After blending, the masterbatch may be processed immediately or pelletized for subsequent use. For example, the blend may be extruded into a water bath and cut into pellet form using a knife or other suitable cutting surface.

Regardless of the particular form of the masterbatch, it is ultimately blended with a melt-extrudable base composition when it is desired to form the nonwoven web. Due to the presence of the carrier resin, the masterbatch may be miscible with the base composition. If the compositions are immiscible, they may simply be blended under shear or modified to improve their interfacial properties. The masterbatch may be blended with the base composition (e.g., polypropylene) before melt extrusion or within the extrusion apparatus itself. The masterbatch may constitute from about 0.5 wt. % to about 25 wt. %, in some embodiments from about 1 wt. % to about 20 wt. %, and in some embodiments, from about 2 wt. % to about 15 wt. % of the blend. The dry liquid concentrates may constitute from about 0.25 wt. % to about 20 wt. %, in some embodiments from about 0.5 wt. % to about 10 wt. %, and in some embodiments, from about 1 wt. % to about 8 wt. % of the blend. The carrier resin may constitute from about 0.25 wt. % to about 20 wt. %, in some embodiments from about 0.5 wt. % to about 10 wt. %, and in some embodiments, from about 1 wt. % to about 8 wt. % of the blend. The liquid additive may be present in the blend in relatively high levels, such as from about 0.0003 wt. % to about 10 wt. %, in some embodiments, from about 0.001 wt. % to about 8 wt. %, and in some embodiments, from about 0.1 wt. % to about 5 wt. % of the blend. Finally, the base composition may constitute at least about 85 wt. %, in some embodiments from about 80 wt. % to about 99 wt. %, and in some embodiments, from about 85 wt. % to about 98 wt. % of the blend.

Exemplary melt-extrudable polymers suitable for use in the base composition may include, for example, polyolefins, polyesters, polyamides, polycarbonates, copolymers and blends thereof, etc. Suitable polyolefins include polyethylene, such as high density polyethylene, medium density polyethylene, low density polyethylene, and linear low density polyethylene; polypropylene, such as isotactic polypropylene, atactic polypropylene, and syndiotactic polypropylene; polybutylene, such as poly(1-butene) and poly(2-butene); polypentene, such as poly(1-pentene) and poly(2-pentene); poly(3-methyl-1-pentene); poly(4-methyl-1-pentene); and copolymers and blends thereof. Suitable copolymers include random and block copolymers prepared from two or more different unsaturated olefin monomers, such as ethylene/propylene and ethylene/butylene copolymers. Suitable polyamides include nylon 6, nylon 6/6, nylon 4/6, nylon 11, nylon 12, nylon 6/10, nylon 6/12, nylon 12/12, copolymers of caprolactam and alkylene oxide diamine, etc., as well as blends and copolymers thereof. Suitable polyesters include poly(lactide) and poly(lactic acid) polymers as well as polyethylene terephthalate, polybutylene terephthalate, polytetramethylene terephthalate, polycyclohexylene-1,4-dimethylene terephthalate, and isophthalate copolymers thereof, as well as blends thereof.

If desired, elastomeric polymers may also be used in the base composition, such as elastomeric polyesters, elastomeric polyurethanes, elastomeric polyamides, elastomeric polyolefins, elastomeric copolymers, and so forth. Examples of elastomeric copolymers include block copolymers having the general formula A-B-A' or A-B, wherein A and A' are each a thermoplastic polymer endblock that contains a styrenic moiety and B is an elastomeric polymer midblock, such as a conjugated diene or a lower alkene polymer. Such copolymers may include, for instance, styrene-isoprene-styrene (S-I-S), styrene-butadiene-styrene (S-B-S), styrene-ethylene-butylene-styrene (S-EB-S), styrene-isoprene (S-I), styrene-butadiene (S-B), and so forth. Commercially available A-B-A' and A-B-A-B copolymers include several different S-EB-S formulations from Kraton Polymers of Houston, Tex. under the trade designation KRATON®. KRATON® block copolymers are available in several different formulations, a number of which are identified in U.S. Pat. Nos. 4,663,220, 4,323,534, 4,834,738, 5,093,422 and 5,304,599, which are hereby incorporated in their entirety by reference thereto for all purposes. Other commercially available block copolymers include the S-EP-S elastomeric copolymers available from Kuraray Company, Ltd. of Okayama, Japan, under the trade designation SEPTON®. Still other suitable copolymers include the S-I-S and S-B-S elastomeric copolymers available from Dexco Polymers of Houston, Tex. under the trade designation VECTOR®. Also suitable are polymers composed of an A-B-A-B tetrablock copolymer, such as discussed in U.S. Pat. No. 5,332,613 to Taylor, et al., which is incorporated herein in its entirety by reference thereto for all purposes. An example of such a tetrablock copolymer is a styrene-poly(ethylene-propylene)-styrene-poly(ethylene-propylene) ("S-EP-S-EP") block copolymer.

Examples of elastomeric polyolefins include ultra-low density elastomeric polypropylenes and polyethylenes, such as those produced by "single-site" or "metallocene" catalysis methods. Such elastomeric olefin polymers are commercially available from ExxonMobil Chemical Co. of Houston, Tex. under the trade designations ACHIEVE® (propylene-based), EXACT® (ethylene-based), and EXCEED® (ethylene-based). Elastomeric olefin polymers are also commercially available from DuPont Dow Elastomers, LLC (a joint venture between DuPont and the Dow Chemical Co.) under the trade designation ENGAGE® (ethylene-based) and from Dow Chemical Co. of Midland, Mich. under the name AFFINITY® (ethylene-based). Examples of such polymers are also described in U.S. Pat. Nos. 5,278,272 and 5,272,236 to Lai, et al., which are incorporated herein in their entirety by reference thereto for all purposes. Also useful are certain elastomeric polypropylenes, such as described in U.S. Pat. Nos. 5,539,056 to Yang, et al. and 5,596,052 to Resconi, et al., which are incorporated herein in their entirety by reference thereto for all purposes.

Generally speaking, the nonwoven web may be formed using any technique known in the art. For example, continuous fibers may be formed by extruding the compounded thermoplastic composition through a die. Although the die may have any desired configuration, it typically contains a plurality of orifices arranged in one or more rows extending the full width of the machine. The orifices may be circular or noncircular in cross-section. The resulting fibers are then drawn, typically by entraining them in a fluid stream (e.g., air) having a sufficiently high velocity. The continuous fibers are cooled in a quenching fluid (e.g., air) prior to drawing. The drawn fibers may then be collected on a moving foraminous surface as a web of entangled fibers.

Figure 1:
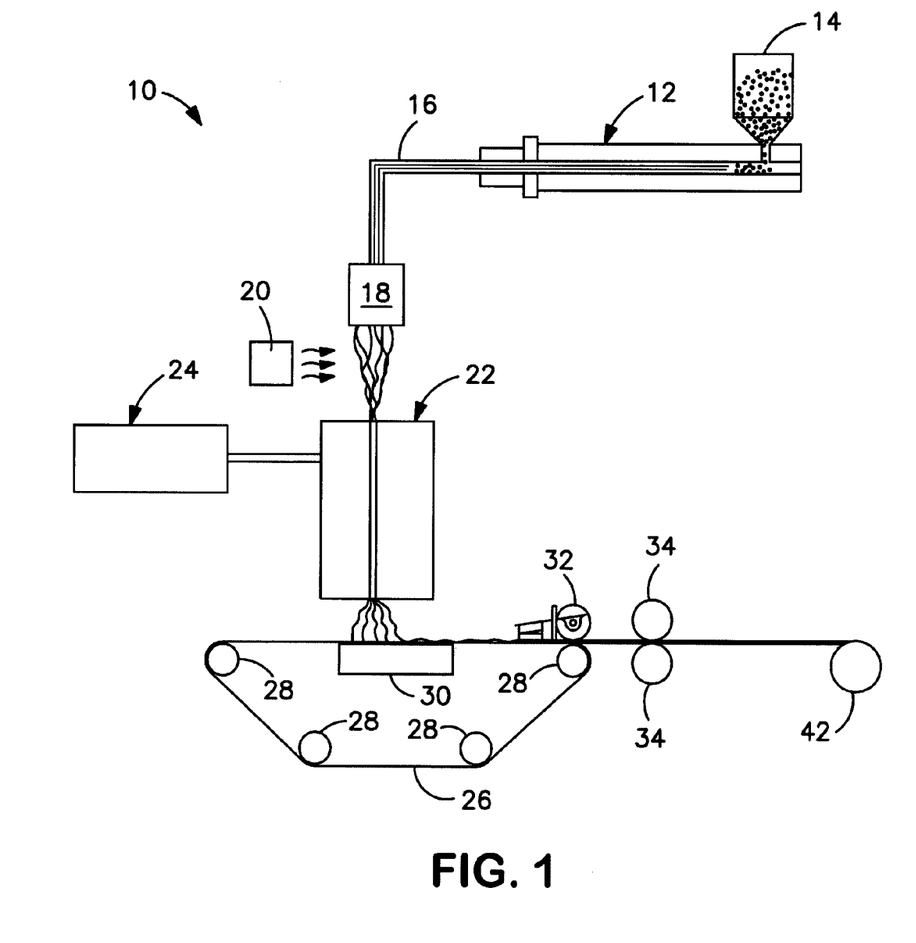
FIG. 1 schematically illustrates a method for forming a nonwoven web in accordance with one embodiment of the present invention.

Referring to FIG. 1, one particular embodiment of a method 10 for forming a nonwoven web is illustrated. In this embodiment, the masterbatch and base compositions are compounded in a hopper 14 and then supplied to an extruder 12. The extruder 12 may employ one or multiple zones operating at a temperature of from about 120° C. to about 200° C., and in some embodiments, from about 145° C. to about 195° C. Typical shear rates range from about 100 seconds$^{-1}$ to about 10000 seconds$^{-1}$, in some embodiments from about 500 seconds$^{-1}$ to about 5000 seconds$^{-1}$, and in some embodiments, from about 800 seconds$^{-1}$ to about 1200 seconds$^{-1}$. The extruded composition then passes through a polymer conduit 16 to a spinneret 18. As the fibers emerge from the spinneret 18, they form a curtain of fibers.

A quench blower 20 is positioned adjacent the curtain of fibers extending from the spinneret 18. Air from the quench blower 20 quenches the fibers extending from the spinneret 18. Such a process generally reduces the temperature of the extruded polymer at least about 100° C. over a relatively short time frame (seconds). This will generally reduce the temperature change needed upon cooling, to preferably be less than 150° C. and, in some cases, less than 100° C. The quench blower 20 typically employs one or more zones operating at a temperature of from about 20° C. to about 100° C., and in some embodiments, from about 25° C. to about 60° C. Such a process generally reduces the temperature of the extruded polymers at least about 100° C. over a relatively short time frame (seconds). After quenching, the fibers are drawn into the vertical passage of a fiber draw unit 22 by a flow of a gas such as air, from the heater or blower 24 through the fiber draw unit. The flow of gas causes the fibers to draw or attenuate which increases the molecular orientation or crystallinity of the polymers forming the fibers. Fiber draw units or aspirators for use in melt spinning polymers are also known. Suitable fiber draw units for use in the process of the present invention include a linear fiber aspirator, such as described in U.S. Pat. No. 3,802,817, a linear draw system, such as described in U.S. Pat. No. 4,340,563, and/or eductive guns, such as described in U.S. Pat. Nos. 3,692,618 and 3,423,266. The fiber draw unit 22 includes an elongate vertical passage through which filaments are drawn by aspirating air entering from the sides of the passage and flowing downwardly through the passage.

An endless foraminous forming surface 26 is positioned below the fiber draw unit 22 and receives the fibers from an outlet opening. The forming surface 26 travels around guide rollers 28. A vacuum 30 positioned below the forming surface 26 to draw the fibers against the forming surface 26 and consolidate the unbonded nonwoven web. The web may be compressed by a compression roller 32 and thermal point bonded by rollers 34, and then wound up onto a roll 42 for further use. For example, an engraved patterned roll and a second bonding roll may be employed as the rollers 34. The engraved roll is patterned in some way so that the web is not bonded over its entire surface, and the second roll may be smooth or patterned. Various patterns for engraved rolls have been developed for functional and/or aesthetic reasons. Exemplary bond patterns include, but are not limited to, those described in U.S. Pat. No. 3,855,046 to Hansen et al., U.S. Pat. No. 5,620,779 to Levy et al., U.S. Pat. No. 5,962,112 to Haynes et al., U.S. Pat. No. 6,093,665 to Sayovitz et al., U.S. Design Pat. No. 428,267 to Romano et al. and U.S. Design Pat. No. 390,708 to Brown, which are incorporated herein in their entirety by reference thereto for all purposes. The nonwoven web may be bonded to have a total bond area of less than about 30% and a uniform bond density greater than about 100 bonds per square inch, and preferably from about 2 to about 30 percent (as determined by conventional optical microscopic methods) and a bond density from about 250 to about 500 pin bonds per square inch. Such a combination of total bond area and bond density may be achieved by bonding the web with a pin bond pattern having more than about 100 pin bonds per square inch that provides a total bond surface area less than about 30% when fully contacting a smooth anvil roll. In some embodiments, the bond pattern may have a pin bond density from about 250 to about 350 pin bonds per square inch and a total bond surface area from about 10% to about 25% when contacting a smooth anvil roll. Of course, any other bonding technique may be utilized in the present invention, such as through-air-bonding, ultrasonic bonding, latex bonding, etc.

Upon formation, the nonwoven web of the present invention may be used in a wide variety of applications. In one particular embodiment, for example, the nonwoven web may be used in an absorbent article. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, and so forth; medical absorbent articles, such as garments, fenestration materials, underpads, bedpads, bandages, absorbent drapes, and medical wipes; food service wipers; clothing articles; and so forth. Materials and processes suitable for forming such absorbent articles are well known to those skilled in the art. Typically, absorbent articles include a substantially liquid-impermeable layer (e.g., outer cover), a liquid-permeable layer (e.g., bodyside liner, surge layer, etc.), and an absorbent core.

In one particular embodiment, the nonwoven web is used to form an outer cover of an absorbent article. For example, a breathable film may be laminated to a nonwoven web formed according to the present invention. In addition, the nonwoven web of the present invention may also be used as an extensible or elastomeric composite material or layer in various components of the absorbent article, such as side barriers, elastomeric diaper ears, waist bands and other components of disposable, absorbent products. Examples of such composite materials may include a continuous filament stretch bonded laminate (CFSBL), a vertical filament laminate (VFL), neck-bonded-laminate (NBL), a stretch-bonded-laminate (SBL), a necked-stretch bonded laminate (NSBL) or a necked-thermal laminate, etc. Exemplary CFSBL, NBL, SBL, and NSBL materials are described in U.S. Pat. Nos. 5,226,992, 4,981,747, 4,965,122, 5,336,545, 5,385,775, 5,414,470, 4,720,415, 4,789,699, 4,781,966, 4,657,802, 4,652,487, 4,655,760, 5,116,662 and 5,114,781, and 6,323,389, all of which are incorporated herein in their entirety by reference thereto for all purposes. Exemplary VFL materials are described in U.S. Patent Application Publication No. 2002/0104608 to Welch, et al., which is incorporated herein in its entirety by reference thereto for all purposes.

Nonwoven webs of the present invention may also be included in multilayer materials or composite materials. Suitable multi-layered materials may include, for instance, spunbond/meltblown/spunbond (SMS) laminates and spunbond/meltblown (SM) laminates. Various examples of suitable SMS laminates are described in U.S. Pat. Nos. 4,041,203 to Brock et al.; 5,213,881 to Timmons, et al.; 5,464,688 to Timmons, et al.; 4,374,888 to Bornslaeger; 5,169,706 to Collier, et al.; and 4,766,029 to Brock et al., which are incorporated herein in their entirety by reference thereto for all purposes. In addition, commercially available SMS laminates may be obtained from Kimberly-Clark Corporation under the designations Spunguard® and Evolution®.

The nonwoven web may also be entangled with another fibrous component using any of a variety of entanglement techniques known in the art (e.g., hydraulic, air, mechanical, etc.). In one embodiment, the nonwoven web is integrally entangled with cellulosic fibers using hydraulic entanglement. A typical hydraulic entangling process utilizes high pressure jet streams of water to entangle fibers to form a highly entangled consolidated fibrous structure, e.g., a nonwoven fabric. Hydraulically entangled nonwoven fabrics of staple length and continuous fibers are disclosed, for example, in U.S. Pat. Nos. 3,494,821 to Evans and 4,144,370 to Boulton, which are incorporated herein in their entirety by reference thereto for all purposes. Hydraulically entangled composite nonwoven fabrics of a continuous fiber nonwoven web and a pulp layer are disclosed, for example, in U.S. Pat. Nos. 5,284,703 to Everhart, et al. and 6,315,864 to Anderson, et al., which are incorporated herein in their entirety by reference thereto for all purposes. The fibrous component of the composite may contain any desired amount of the resulting substrate. The fibrous component may contain greater than about 50% by weight of the composite, and in some embodiments, from about 60% to about 90% by weight of the composite. Likewise, the nonwoven web may contain less than about 50% by weight of the composite, and in some embodiments, from about 10% to about 40% by weight of the composite.

The present invention may be better understood with reference to the following examples.

Materials

Liquid Additive:

SilQuest PA-1® is a silicone liquid additive available from GE Silicones having the following structure:

wherein,

R is an alkyl group;

$R^1$ is a monovalent organic group containing at least one ethylene oxide group, vicinal epoxy group, or amino group; and x and y are independently selected from the group of positive integers.

Filler Particles:

Hi-Sil® ABS is available from PPG Industries and is a white precipitated silica powder with a uniform spherical shape and a median agglomerate diameter of 20 micrometers. The silica powder is amorphous in structure and highly porous with a surface area of 150 $m^2$/g.

Calcium carbonate particles were employed that are available from Omya, Inc. of Proctor, Vt. under the designation Snowhite® 3, which have a specific surface area of 3.2 meters squared per gram and a median diameter of 3.2 micrometers.

Calcium carbonate particles were employed that are available from Omya, Inc. of Proctor, Vt. under the designation Omycarb® 2 SST, which have a median diameter of 2 microns and are treated with less than 2 wt. % stearic acid.

Carrier Resin:

A polypropylene homopolymer was employed that is available from Basell North America, Inc. under the designation "Prof-fax™ 6301" (reactor grade). The resin has a melt flow rate of 12 (at 230° C. and 2.16 kg), a density of 0.9 grams per cubic centimeter, and has a spherical particle form.

A polypropylene homopolymer was employed that is available from ExxonMobil under the designation "PP3155." The resin has a melt flow rate of 35 (at 230° C. and 2.16 kg), a density of 0.9 grams per cubic centimeter, and a polydispersity index of less than 3.0.

Masterbatch Preparation

The dry liquid concentrates ("DLC") were prepared using conventional techniques, i.e., by mixing the particles and liquid additive at room temperature. The following samples were formed:

| DLC Sample | Snowhite® 3 (wt. %) | Omyacarb® 2 SST (wt. %) | HiSil® ABS (wt. %) | SilQuest® PA-1 (wt. %) |
|---|---|---|---|---|
| 1 | 93.00 | — | — | 7.00 |
| 2 | — | 93.00 | — | 7.00 |
| 3 | 96.25 | — | — | 3.75 |
| 4 | — | 96.25 | — | 3.75 |
| 5 | — | — | 61.00 | 39.00 |

Figure 2:
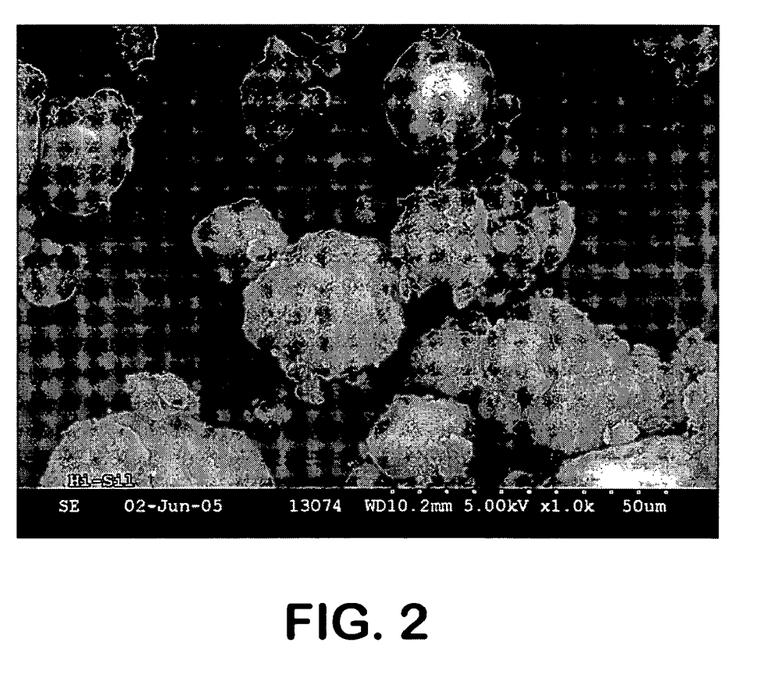
FIG. 2 is a scanning electronic microphotograph (WD=10.2 mm, 5.00 kv, a bar to provide scale is included) of the silica particles used in the Examples.
Figure 3:
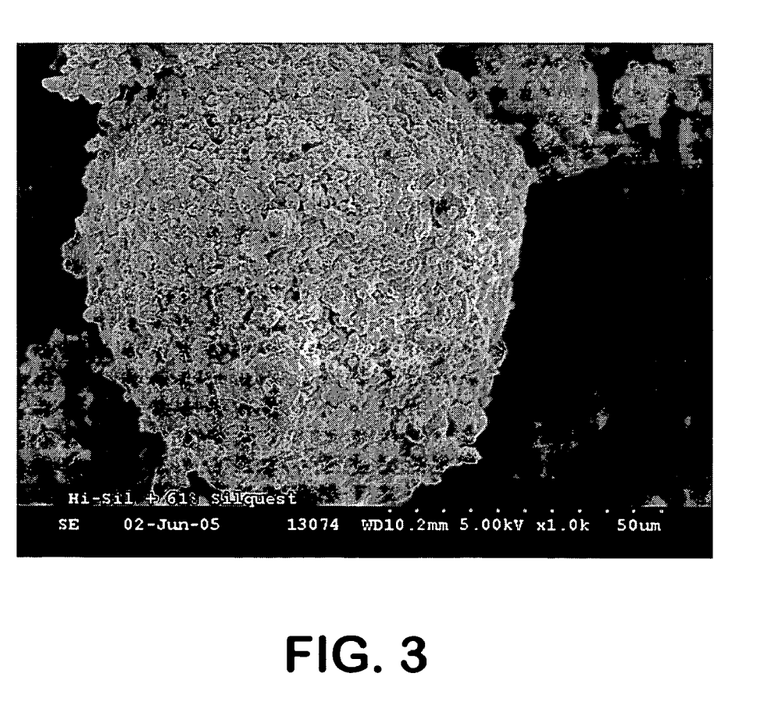
FIG. 3 is a scanning electronic microphotograph (WD=10.2 mm, 5.00 kv, a bar to provide scale is included) of a dry liquid concentrate formed in the Examples that contained 61 wt. % of a SilQuest® PA-1 liquid additive and 39 wt. % HiSil® ABS particles.

An SEM microphotograph of DLC Sample 5 is shown in FIG. 3. In comparison, an SEM microphotograph of only the HiSil® ABS particles is shown in FIG. 2. From these microphotographs, it is evident that the SilQuest® PA-1 was readily loaded onto the particles.

Masterbatches were then formed by compounding the dry liquid concentrate samples with a carrier resin as set forth below:

| Masterbatch | PP3155 (wt. %) | Pro-fax™ 6301 (wt. %) | DLC Sample 1 (wt. %) | DLC Sample 2 (wt. %) | DLC Sample 5 (wt. %) |
|---|---|---|---|---|---|
| A | 50 | — | — | 50 | — |
| B | 50 | — | — | — | 50 |
| C | — | 50 | 50 | — | — |
| D | — | 50 | — | — | 50 |

Each masterbatch was compounded using a 1.5" twin screw extruder (L:D ratio of greater than 30). The extruder was allowed to purge clean for 30 minutes before introduction of each example material. A more detailed description of the manner in which each masterbatch was prepared is set forth below.

Masterbatch A

The dry liquid concentrates were first dry blended with the PP3155 resin.

The materials were added together to yield a 50 wt. % PP3155 and 50 wt. % DLC Sample 2 (93 wt. % Omyacarb® 2 SST and 7 wt. % SilQuest® PA-1). The materials were physically mixed for 5 minutes until uniform in consistency. The mixture was then gravity fed into the extruder. The melt temperature of the material remained at 340° F. with a stable pack pressure of 260 pounds per square inch. The material was successfully extruded and passed through a water bath before pelletization. Based on the feed mixture, the average composition of the resulting pellets was as 46.25 wt. % Omyacarb® 2 SST, 50 wt. % PP3155, 3.75 wt. % SilQuest® PA-1.

Masterbatch B

The dry liquid concentrates were dry blended with the PP3155 resin. The materials were added together to yield a 50 wt. % PP3155 and 50 wt. % DLC Sample 5 (61 wt. % HiSil® ABS and 39 wt. % SilQuest® PA-1). The materials were physically mixed for 5 minutes until uniform in consistency. The mixture was then gravity fed into the extruder. During gravity feeding, the resin pellets quickly separated from the dry liquid concentrates in the dry blend. The material could not be uniformly introduced into the extruder, and was hand metered into the hopper. The melt temperature remained at 340° F. with a stable pack pressure of 260 pounds per square inch. The material was successfully extruded and passed through a water bath before successful pelletization. Based on the feed mixture, the average final composition of the material was 50 wt. % PP3155, 19.5 wt. % HiSil® ABS, and 30.5 wt. % SilQuest® PA-1.

Masterbatch C

The dry liquid concentrates were dry blended with the Pro-fax™ 6301 resin. The materials were added together to yield a 50 wt. % Pro-fax™ 6301 and 50 wt. % DLC Sample 1 (93 wt. % Snowhite® 3 and 7 wt. % SilQuest® PA-1). The materials were physically mixed for 5 minutes until uniform in consistency. The mixture was then gravity fed into the extruder. The melt temperature of material remained at 340° F. with a stable pack pressure of 260 pounds per square inch. The material had very little melt strength and was unable to be pelletized. Based on the feed mixture, the average final composition of the material was 46.25 wt. % Snowwhite® 3, 50 wt. % Pro-fax™ 6301, 3.75 wt/% SilQuest PA-1®.

Masterbatch D

Figure 4:
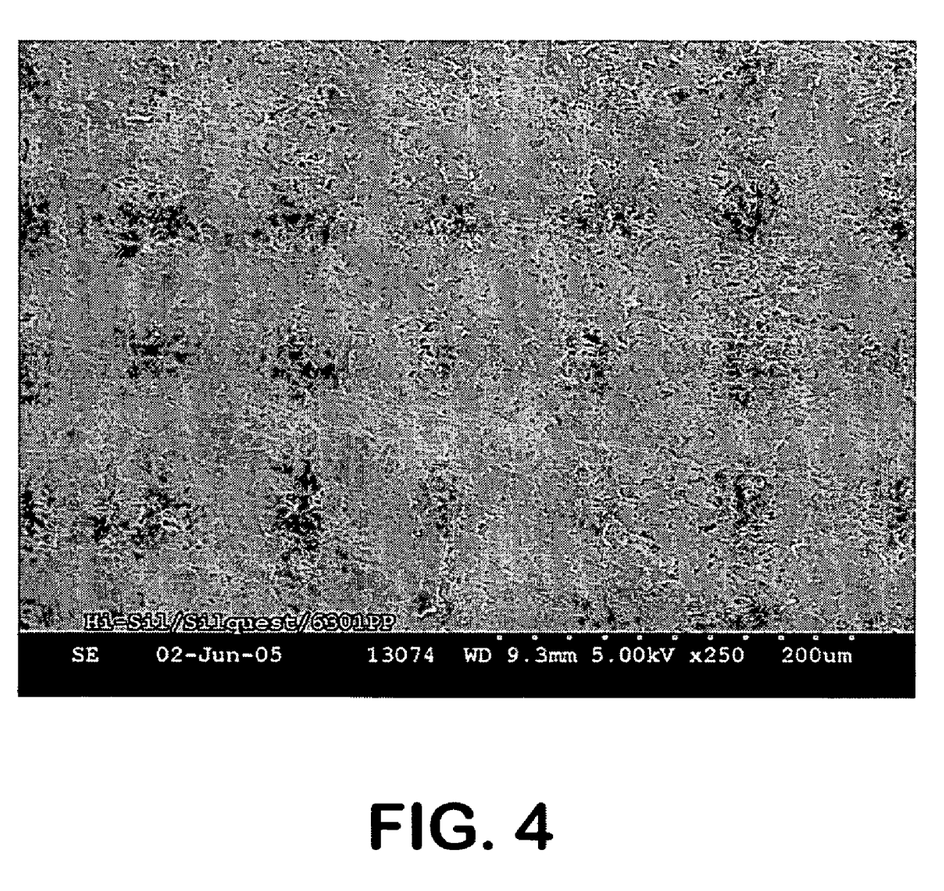
FIG. 4 is a scanning electronic microphotograph (WD=9.3 mm, 5.00 kv, a bar to provide scale is included).

To avoid separation of the resin and dry liquid concentrate as described in Masterbatch B, a reactor grade polypropylene resin was selected, i.e., Pro-fax™ 6301 resin. The materials were weighed and blended to yield a 50 wt. % Pro-fax™ 6301 and 50 wt. % DLC Sample 5 (61 wt. % HiSil® ABS and 39 wt. % SilQuest® PA-1) mixture. The materials were physically mixed for 5 minutes until uniformly blended. The mixture was then gravity fed into the extruder. Using this particular carrier resin, the material was successfully metered in a controlled and uniform manner into the extruder system. The melt temperature remained at 340° F. with a stable filter pack pressure of 260 pounds per square inch. The material was extruded, passed through a water bath and then pelletized Based on the feed mixture, the average final composition of the material was 50 wt. % Pro-fax™ 6301, 19.5 wt. % HiSil® ABS, and 30.5 wt. % SilQuest® PA-1. An SEM microphotograph of the material is shown in FIG. 4. As illustrated, the silica particles were pulverized during processing and reduced in particle size to about 1 micrometer or less.

EXAMPLE

The ability to form a spunbond web in accordance with the present invention was demonstrated. Initially, various control samples (identified as Controls 1-5) were formed from a PP3155 base polymer, titanium dioxide, and a masterbatch that contained 97 wt. % PP3155 and 3 wt. % SilQuest® PA-1. Besides the control samples, a sample (identified as Sample 1) was also formed that contained a PP3155 polymer, titanium dioxide, and Masterbatch D, which contained 50 wt. % Pro-fax™ 6301 and 50 wt. % DLC Sample 5 (61 wt. % HiSil® ABS and 39 wt. % SilQuest® PA-1). Each sample was extruded using an extruder screw having a 4.5" O.D. and a 32:1 L/D. The extruder also had a spherical dynamic mixer at the end of the screw with a matching barrel spool adapter. The extrusion process was substantially similar to that described herein. The conditions and equipment remained constant for each sample, with the following exceptions:

|  | Control 1 | Control 2 | Control 3 | Control 4 | Control 5 | Sample 1 |
|---|---|---|---|---|---|---|
| Base Polymer (wt. %) | 99.00 | 82.00 | 92.50 | 89.00 | 89.00 | 95.70 |
| TiO$_2$ (wt. %) | 1.00 | 1.00 | 1.00 | 1.00 | 1.00 | 1.00 |
| Masterbatch (wt. %) | 0.00 | 17.00 | 7.00 | 10.00 | 10.00 | 3.30 |
| SilQuest ® PA-1 (wt. %) | 0.51 | 0.51 | 0.21 | 0.30 | 0.30 | 1.01 |
| Throughput (grams per hole per minute) |  |  | 0.5 |  |  |  |
| Pack Pressure (lbs/in$^2$) | 508 | 439 | 497 | 485 | 509 | 535 |
| Bond Roll Temp. (° F.) |  |  | 325 |  |  |  |
| Bond Roll Pressure (lbs/in) |  |  | 360 |  |  |  |
| F.D.U Pressure (lbs/in$^2$) |  |  | 7 |  |  |  |
| Basis Wt. (osy) |  |  | 0.50 |  |  |  |
| Extruder Zone 1 (° F.) |  |  | 370 |  |  |  |
| Extruder Zone 2 (° F.) |  |  | 380 |  |  |  |
| Extruder Zone 3 (° F.) |  |  | 390 |  |  |  |
| Extruder Zone 4 (° F.) |  |  |  | 430 |  | 420 |
| Extruder Zone 5 (° F.) |  |  |  | 440 |  | 430 |
| Extruder Zone 6 (° F.) |  |  |  | 450 |  | 440 |
| Pack Temp. (° F.) |  |  |  | 450 |  | 440 |
| Pipe Temp. (° F.) |  |  |  | 450 |  | 440 |
| Melt Temp. (° F.) |  |  |  | 440 |  | 430 |

The concentrates were easily fed into the melt stream. Upon observation, it was determined that the spunbond samples were uniform and each sample that contained the liquid additive had a softer hand than the control.

While the invention has been described in detail with respect to the specific embodiments thereof, it will be appreciated that those skilled in the art, upon attaining an understanding of the foregoing, may readily conceive of alterations to, variations of, and equivalents to these embodiments.

Accordingly, the scope of the present invention should be assessed as that of the appended claims and any equivalents thereto.

What is claimed is:

1. A method for forming a nonwoven web, the method comprising:
compounding a masterbatch with a base composition to form a blend, wherein the masterbatch comprises a plurality of dry liquid concentrates blended with a carrier resin, the dry liquid concentrates constituting from about 20 wt. % to about 80 wt. % of the masterbatch, wherein the dry liquid concentrates are formed from filler particles loaded with a liquid additive, the liquid additive constituting from about 10 wt. % to about 80 wt. % of the dry liquid concentrates and the filler particles constituting from about 20 wt. % to about 90 wt. % of the dry liquid concentrates;
melt extruding the blend to form fibers; and
depositing the fibers onto a forming surface.

2. The method of claim 1, wherein the filler particles are selected from the group consisting of silica, alumina, zirconia, magnesium oxide, titanium dioxide, iron oxide, zinc oxide, zeolites, silicates, titanates, zirconates, clays, calcium carbonate, barium sulfate, carbon black, and organic pigments.

3. The method of claim 1, wherein the filler particles comprise silica.

4. The method of claim 1, wherein the filler particles have an average size of less than about 500 micrometers and a surface area of from about 50 to about 1000 square meters per gram.

5. The method of claim 1, wherein the filler particles have an average size of less than about 100 micrometers and a surface area of from about 100 to about 250 square meters per gram.

6. The method of claim 1, wherein the liquid additive has a kinematic viscosity of from about 1 to about 150,000 centistokes.

7. The method of claim 1, wherein the liquid additive has a kinematic viscosity of from about 500 to about 10,000 centistokes.

8. The method of claim 1, wherein the liquid additive is a skin care additive.

9. The method of claim 8, wherein the skin care additive includes dimethicone.

10. The method of claim 1, wherein the liquid additive contains an organopolysiloxane having the following general formula:

wherein, $x \geq 1$;
$y \geq 0$; and
each R is individually selected from the group consisting of unsubstituted and substituted monovalent hydrocarbon groups containing from 1 to 20 carbon atoms.

11. The method of claim 1, wherein the liquid additive constitutes from about 25 wt. % to about 50 wt. % of the dry liquid concentrates.

12. The method of claim 1, wherein the dry liquid concentrates constitute from about 40 wt. % to about 60 wt. % of the masterbatch.

13. The method of claim 1, wherein the carrier resin constitutes from about 20 wt. % to about 80 wt. % of the masterbatch.

14. The method of claim 1, wherein the carrier resin constitutes from about 40 wt. % to about 60 wt. % of the masterbatch.

15. The method of claim 1, wherein the carrier resin contains an amorphous polymer, a semi-crystalline polymer, or a combination thereof.

16. The method of claim 1, wherein the carrier resin contains a semi-crystalline polymer selected from the group consisting of ethylene-based polymers, propylene-based polymers, and combinations thereof.

17. The method of claim 16, wherein the semi-crystalline polymer is a propylene-based polymer having a melt flow rate of from about 5 to about 50 grams per 10 minutes, measured at a force of 2160 grams and temperature of 230° C. in accordance with ASTM Test Method D1238-E.

18. The method of claim 1, wherein the base composition comprises a propylene-based polymer.

19. The method of claim 1, wherein the masterbatch constitutes from about 0.5 wt. % to about 25 wt. % of the blend.

20. The method of claim 1, wherein the masterbatch constitutes from about 2 wt. % to about 15 wt. % of the blend.

21. The method of claim 1, wherein the filler particles constitute from about 40 wt. % to about 80 wt. % of the dry liquid concentrates.

22. The method of claim 1, wherein the filler particles constitute from about 50 wt. % to about 75 wt. % of the dry liquid concentrates.

23. The method of claim 1, wherein the liquid additive constitutes from about 20 wt. % to about 60 wt. % of the dry liquid concentrates.

24. The method of claim 1, wherein the liquid additive constitutes from about 0.0003 wt. % to about 10 wt. % of the blend.

25. The method of claim 1, wherein the liquid additive constitutes from about 0.1 wt. % to about 5 wt. % of the blend.

26. The method of claim 1, wherein the carrier resin constitutes from about 0.25 wt. % to about 20 wt. % of the blend.

27. The method of claim 1, wherein the base composition constitutes at least about 85 wt. % of the blend.

* * * * *